(12) United States Patent
West

(10) Patent No.: US 10,525,198 B2
(45) Date of Patent: Jan. 7, 2020

(54) FLOW METER FOR INTRAVENOUS LIQUIDS

(71) Applicant: Jonathan Charles Devlin West, Chesham (GB)

(72) Inventor: Jonathan Charles Devlin West, Chesham (GB)

( * ) Notice: Subject to any disclaimer, the term of this patent is extended or adjusted under 35 U.S.C. 154(b) by 52 days.

(21) Appl. No.: 15/568,049

(22) PCT Filed: Aug. 7, 2015

(86) PCT No.: PCT/GB2015/000233
§ 371 (c)(1),
(2) Date: Oct. 20, 2017

(87) PCT Pub. No.: WO2016/170296
PCT Pub. Date: Oct. 27, 2016

(65) Prior Publication Data
US 2018/0117247 A1    May 3, 2018

(30) Foreign Application Priority Data

Apr. 21, 2015 (GB) .................................. 1506771.3

(51) Int. Cl.
*A61M 5/168* (2006.01)
*G01F 1/37* (2006.01)
(Continued)

(52) U.S. Cl.
CPC ........ *A61M 5/16886* (2013.01); *A61M 5/165* (2013.01); *A61M 5/1689* (2013.01);
(Continued)

(58) Field of Classification Search
USPC .......................................... 222/154; 137/559
See application file for complete search history.

(56) References Cited

U.S. PATENT DOCUMENTS 4,136,692 A * 1/1979 Goldowsky ....... A61M 5/16886
137/551
4,291,693 A * 9/1981 Todd .................... A61M 5/162
137/551

(Continued)

FOREIGN PATENT DOCUMENTS

DE     4419369 A1    12/1994

OTHER PUBLICATIONS

International Search Report and Written Opinion issued in counterpart International Application No. PCT/GB2015/000233 dated Jan. 18, 2016.

(Continued)

*Primary Examiner* — Nathan R Price
*Assistant Examiner* — John A Doubrava
(74) *Attorney, Agent, or Firm* — Brian J. Colandreo; Jeffrey T. Placker; Holland & Knight LLP

(57) ABSTRACT

A flow meter for intravenous liquids comprising a vertical inlet passage (2), a parallel indicating chamber (9), a 'U' shaped flow-resistant liquid passage (6), and an exit chamber (11). Liquid to be dispensed enters the inlet passage (2) via inlet (5) and moves down the passage to a junction with both the 'U' shaped flow-resistant passage (6), and the indicator passage. From the junction, the liquid rises up the indicator passage to a height proportional to the flow rate set by an external flow meter, and also through the flow resistant passage, which has an outlet (8) that delivers the liquid to the exit chamber (11) and from there to a patient through an outlet (12). The meter may be formed by an assembly of two injection molded components, thus reducing manufacturing costs.

16 Claims, 2 Drawing Sheets

(51) Int. Cl.
*G01F 1/52* (2006.01)
*A61M 5/165* (2006.01)

(52) U.S. Cl.
CPC ............... *G01F 1/375* (2013.01); *G01F 1/52* (2013.01); *A61M 2205/3382* (2013.01); *A61M 2205/584* (2013.01)

(56) References Cited

U.S. PATENT DOCUMENTS 4,523,464 A * 6/1985 Pedersen ........... A61M 5/16886
73/216
5,352,213 A 10/1994 Woodard

OTHER PUBLICATIONS

International Preliminary Report on Patentability issued in counterpart International Application No. PCT/GB2015/000233 dated Apr. 4, 2017.

* cited by examiner

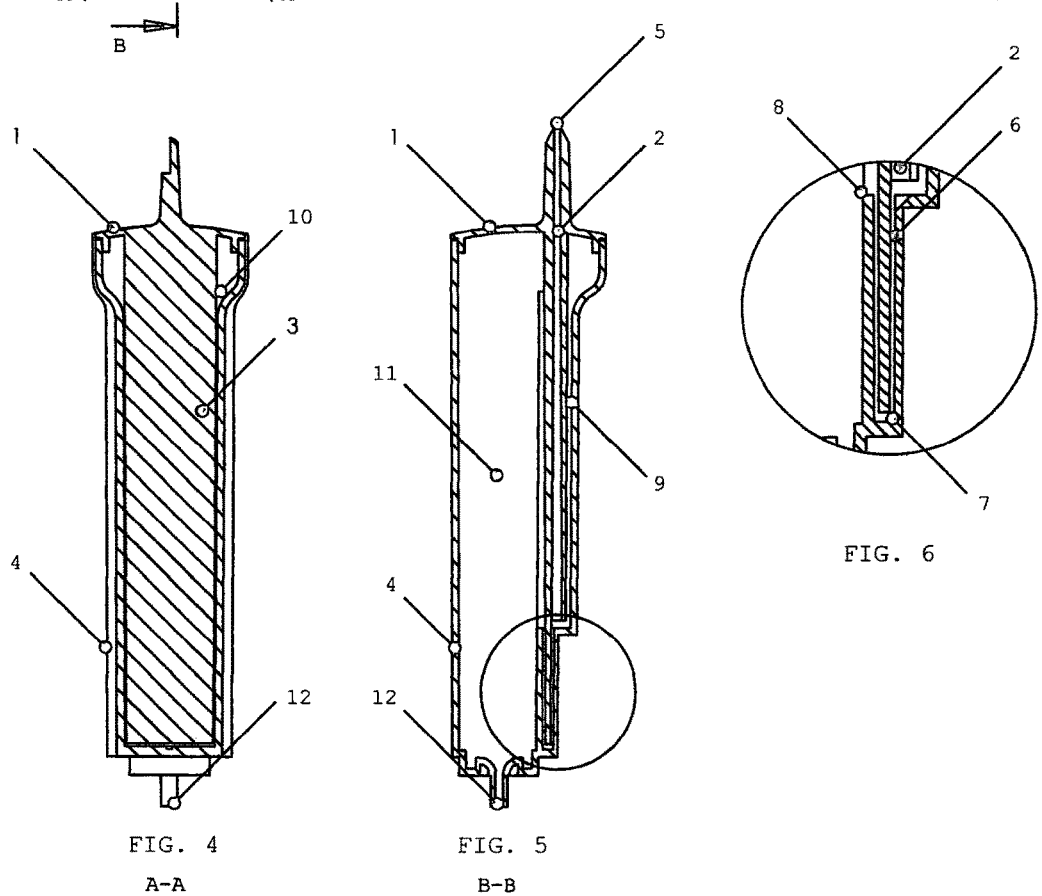

FLOW METER FOR INTRAVENOUS LIQUIDS

CROSS-REFERENCE TO RELATED APPLICATIONS

The subject application is a U.S. National Stage application of International Application No. PCT/GB2015/000233, filed on Aug. 7, 2015, which claims the priority of Great Britain Patent Application No. 1506771.3, filed Apr. 21, 2015. The contents of both applications are herein incorporated by reference in their entirety.

FIELD OF INVENTION

This invention relates generally to flow indicating devices and more particularly to improved flow meters for the administration of intravenous solutions.

BACKGROUND OF THE INVENTION

Intravenous administration sets are generally used to infuse various types of solutions into a patient. A set provides a means of controlling the sterile passage of a physiological liquid (e.g. saline, glucose solution etc) from a rigid or flexible supply container into a patient. Conventional intravenous administration sets feature a closed chamber with a nozzle, creating drops when the liquid flows. The purpose of this is to enable the liquid flow rate to be calculated by counting the number of drops per unit time. This can be time consuming and inaccurate, as drop size is not constant, and the conversion of drop timing to liquid flow rate can be difficult.

A number of well established flow meter designs have been adapted for use in intravenous liquid administration.

Variations on the rotameter design (e.g. U.S. Pat. No. 3,587,313) employ a small ball of proper specific gravity (usually greater than the liquid, though it may also be a float in some designs) positioned within a tapered vertical tube. The ball is pushed towards the larger cross sectional area of the indicating tube as the liquid flows; the position of the ball is indicative of the liquid flow rate. Though these devices enable more accurate regulation and adjustment of flow rate, they are expensive to manufacture due to the high tolerances required, as well as the potentially complex assembly of components.

Another type of flow meter device (U.S. Pat. No. 2,479,786A) employs a tube arranged vertically, with the liquid inlet at the top, and with a short portion bent back upon itself. A small orifice in the wall of the tube at the bend allows liquid to flow downwards. This arrangement is encased within a larger sealed container having an outlet to further tubing leading to the patient. Liquid flow in the tube, combined with the resistance to flow caused by the orifice, causes the liquid level in the shorter portion to rise to a level proportional to the flow rate. This design is simpler than the rotameter variants, but is inaccurate at low flow rates, and it is difficult to manufacture multiple units with consistent geometry, further affecting calibration and accuracy.

Another type of flow meter device (U.S. Pat. No. 4,136,692A) uses a similar principle, replacing the bent tube with two connected tubes within a larger sealed tube with an outlet to the patient. The small orifice in U.S. Pat. No. 2,479,786A is replaced with highly accurate orifice disks of minimal thickness (0.001 in). This has the effect of minimising any effects of changing temperature and viscosity on accuracy, but the design remains a relatively complex assembly of small parts, resulting in manufacturing costs higher than a standard liquid administration set.

Accordingly, the primary objective of the present invention is to provide a flow meter device that is easier, quicker, and more accurate to use than the standard administration set that requires the counting of drops, and is comparable in cost to manufacture.

DISCLOSURE OF INVENTION

This objective is accomplished by a flow meter device of the present invention which comprises a vertical liquid inlet passage (2) with an upper end in communication with a liquid container and its lower end in communication with an adjoining vertical indicating chamber (9) with an open upper end, and a flow-resistant liquid passage (6) at the lower end, with the inlet passage, indicating chamber and flow-resistant liquid passage being contained within an outer housing formed by the top component (1) and the base component (4) having an outlet (12) at its lower portion.

A distinguishing characteristic of the flow meter of this invention is the provision of a flow-resistant liquid passage forming a 'U'-shaped bend (7), positioned at the lower end of the indicating chamber (9).

Liquid flowing in the liquid inlet passage will encounter resistance due to the flow-resistant liquid passage (6). The indicating chamber is connected to the inlet passage upstream (and preferably immediately upstream) of the flow resistant passage and so liquid will flow from the inlet passage into the adjoining indicating chamber (9) and the liquid level in the indicating chamber will rise to a height proportional to the liquid flow rate through the device, as regulated by an external flow control device (typically a manual 'roller clamp'). The indicating chamber (9) is marked with calibrated scales to give a clear reading of liquid flow rate. At high flow rates, the liquid level may exceed the height of the indicating chamber, and so the open upper end (10) of the indicating chamber may provide an overflow to allow liquid to flow freely through the device.

Devices that rely on the same principle of a liquid head being proportional to flow through an orifice have thus far been unreliable at low flow rates (below 50 ml/hour), and/or have required high tolerances and expensive manufacturing costs.

A distinguishing characteristic of the present invention is the provision of the flow-resistant liquid passage forming a 'U' shape, which may have a chamfered inlet and outlet, as described later. This allows improved accuracy and consistency of indicated flow, even at low flow rates, and can be manufactured within standard injection moulding tolerances (±0.05 mm). The 'U' shape, along with the chamfered inlet and outlet, also provides that, when flow is stopped by the operator, the flow-resistant liquid passage does not dry out and remains wet. This prevents the build up of solid deposits in the flow-resistant liquid passage if the liquid evaporates, which may affect the cross sectional area of the flow-resistant liquid passage and thus affect resistance to flow and introduce error in the reading of the liquid flow rate in the indicating chamber.

The flow-resistant liquid passage of the present invention provides resistance to liquid flow and an associated drop in pressure as described by the Hagen-Poiseuille equation for liquid flow through a pipe:

$$\Delta P = 8\mu L Q / \pi r^4$$

where $\Delta P$ is the pressure loss

L is the length of pipe

μ is the dynamic viscosity
Q is the volumetric flow rate
r is the radius
π is the mathematical constant Pi The pressure drop is dependent on (among other factors) pipe length and radius or, for non-circular pipes, the cross-sectional area. The equivalent resistance of the small orifices used in flow meters described in the prior art may be provided in a device of the present invention by a flow-resistant liquid passage (6) of sufficient length and cross section.

The cross section is typically small and therefore more prone to tolerance issues in manufacture; increasing the length of the passage may mitigate the effect of this problem by allowing the flow-resistant passage to have a larger cross section by suitably setting the passage length.

The provision of the inlet passage (2), indicating chamber (9), flow-resistant liquid passage (6) and exit chamber (11) can be achieved by a simple assembly of two parts ((1) and (4)), one fitting into the other. Each part may be a simple two-piece mould. In one embodiment, the flow-resistant passage may be formed by providing one part with a bore and the other part with an insert that can be inserted into the bore to restrict its flow cross section, which makes it easier to achieve the required consistent tolerances than manufacturing one part with the complete flow-resistant passage. In one embodiment, the insert forms a barrier that divides the bore so as to form a U-shaped flow-resistant passage with the liquid flowing firstly down the bore on one side of the barrier before passing under the bottom of the barrier, which does not reach the bottom of the bore, and up the bore on the other side of the barrier. If the bore is circular, the resulting flow-resistant liquid passage is semi-circular in cross section. Though many combinations of pipe cross sectional area and length can achieve the correct pressure drop needed for a readable scale of acceptable length (a practical scale could span 60 mm-130 mm, but preferably is around 80 mm), a manifestation of the present invention uses a semi-circular cross section of 0.5 mm radius with a passage length of 46 mm. As can be seen from the Hagen-Poiseille equation above, an increase in cross section would necessitate a very substantial increase in passage length; similarly a decrease in cross section would drastically reduce the necessary passage length. The selection of dimensions stated are a compromise to allow a relatively wide passage cross section to reduce the effects of tolerance in manufacture, yet keep a passage length that is still practical (e.g. <60 mm). Combinations of dimensions must be defined using the above equation.

This geometry allows the present invention to be manufactured in the same manner as existing liquid administration sets and should be comparable in price despite offering this increased functionality.

BRIEF DESCRIPTION OF DRAWINGS

For a more complete explanation of the present invention and the technical advantages thereof, reference is now made to the following description and the accompanying drawings in which:

FIG. 3 shows a plan view of the liquid flow meter with cross section lines;

FIG. 4 is a cross-sectional view (taken along line A-A of FIG. 3), showing the overflow of the indicating chamber;

FIG. 5 is a cross-sectional view (taken along line B-B of FIG. 3), showing the inlet passage, indicating chamber, flow-resistant liquid passage and exit chamber formed by the base component;

FIG. 6 is an enlarged sectional view of the flow-resistant liquid passage also shown in FIG. 5.

BEST MODE FOR CARRYING OUT THE INVENTION

Figures 1, 2:
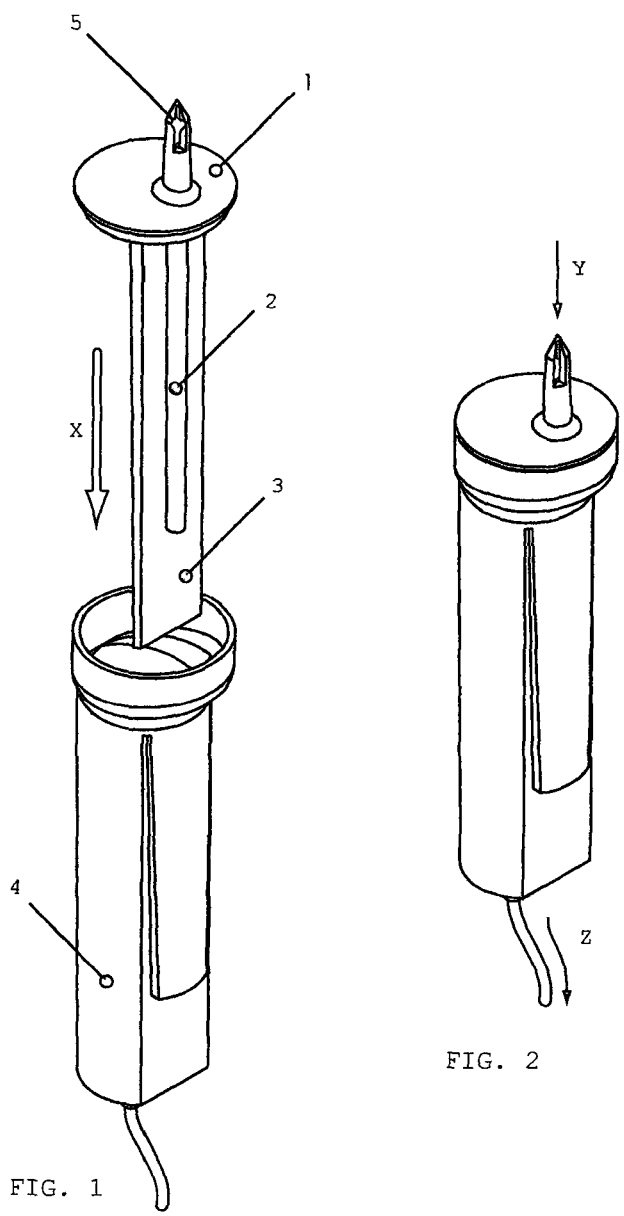
FIG. 1 shows the assembly process of joining the two components of the present invention, similar to the assembly of a standard intravenous liquid administration set.
FIG. 2 shows the fully assembled liquid flow meter.

Referring to the drawings, a preferred embodiment of the present invention is illustrated in FIGS. 1 and 2. The device is assembled in manufacture by inserting (see arrow X in FIG. 1) the top (1), featuring an inlet passage (2) which may be fitted with a filter (not shown) at its lower outlet, and a dividing panel (3), into the base (4), the base being manufactured from a clear material (preferably a medical grade rigid plastic), and having a corresponding recess to accommodate the dividing panel. The finished assembly may be bonded by heat sealing, ultrasonic welding or solvent cementing. FIG. 2 shows the assembled flow meter for liquid flowing from a supply container (not shown) into the circulatory system of a patient (not shown). The liquid container is either a flexible bag or vented rigid container.

The penetrant with liquid inlet (5) is inserted into the supply container (not shown) to define an inlet passage (2) for liquid flow (see arrow Y) from the supply container downwards under gravity, and regulated by an external flow control device (typically a manual 'roller clamp', positioned downstream of the device). This passage may be fitted with a filter (not shown) at its lower outlet in order to prevent particles in the liquid being deposited in the flow-resistant liquid passage ((6) in FIG. 6), which might affect the device reliability.

The lower part of the inlet passage (2) is in communication with both an indicating chamber (9) and a flow-resistant liquid passage (6). The flow-resistant liquid passage (6) provides sufficient resistance to liquid flow such that liquid rises in the indicating chamber (9) to a height proportional to the flow rate. A scale of calibrated indices may be placed alongside the indicating chamber (9). The minimum width of the indicating chamber is sufficiently wide (>1 mm, preferred width 1.5 mm) to reduce the effects of capillary action, yet sufficiently narrow to ensure that the response of the liquid column quickly follows any flow changes made by the operator by the use of the external flow control device. This width is reliably maintained by the secure interference fit between the top component (1) and the base component (4).

The insertion of the top component (1) with the dividing panel (3) into the base (4) forms the flow-resistant liquid passage (6) with a chamfered inlet, a 'U' shaped bend (7) and a chamfered outlet (8). The slight taper on the dividing panel (3) improves the interference fit necessary to form a sufficient seal, as well as serving as a draft angle to help the injection moulding process. The dimensions of the flow-resistant liquid passage are maintained reliably by this interference fit; the dividing panel (3) providing a seal against the corresponding recess in the base component (4) into which the flow-resistant liquid passage is moulded. Upon exit from this outlet (8), liquid enters the exit chamber (11) formed by the base component (4) and top component (1) and flows out through the main outlet (12) (see arrow Z in FIG. 2) which may accommodate a standard filter (not necessary if one is fitted to the inlet passage) into the length of tubing connecting the device to an intravenous cannula inserted into the patient.

At higher flow rates (for example, greater than 250 ml/hr), the liquid level in the indicating chamber (9) may rise above an overflow ((10) in FIG. 4), and thus liquid may flow into the exit chamber (11) formed by the base component (4) and top component (1), and then out through the main outlet (12). In this manner, a readable scale from 0-250 ml/hr may be provided on the indicating chamber (9), but flow rates of 3000 ml/hr or more (necessary during resuscitation attempts) may also be achieved by the device; the scale being unnecessary at such high flow rates. In a further embodiment of the present invention, the overflow (10) may be so shaped as to produce drops as liquid flows into the exit chamber (11). Thus, if control of flow at rates greater than those measurable in the indicating chamber is required, drops may be counted as per the current method of measuring flow rate.

When the liquid flow rate is such that the liquid level exceeds the height of the indicating chamber (9), and then flow is stopped by the operator, the liquid contained in the full indicating chamber (9) flows through the flow-resistant liquid passage (6) into the exit chamber (11) formed by the base component (4) and the top component (1). As the main liquid outlet is effectively blocked by the operator (e.g. by closing a roller clamp to stop flow), the exit chamber (11) begins to fill with the remaining liquid flowing out of the indicating chamber (9). The outlet of the flow-resistant liquid passage (8) is positioned at sufficient height (greater than 20 mm) above the main outlet (12) such that as the exit chamber (11) fills with the remaining liquid from the indicating chamber (9), the liquid height does not reach this outlet. This feature prevents any liquid flow back through the flow-resistant liquid passage (6) when the operator has stopped the liquid flow; this would otherwise result in liquid resting in equilibrium in the indicating chamber (9) when flow has stopped, introducing a false level and a 'zero' error.

The design of the present invention dictates that as liquid flows through the liquid inlet passage (2), flow-resistant liquid passage (6) and indicating chamber (9), no drops are formed. This avoids the problem of irregular drop size affecting the height of liquid in the indicating chamber, as well as any problems introduced by the need to break the surface tension of drops at low flow rates.

In another embodiment of the present invention, a small float in the indicating chamber (9) rises and falls with the liquid level, facilitating the reading of flow rate. The float may provide greater visual contrast (e.g. bright colour). In this embodiment, the overflow outlet (10) at the top of the indicating chamber (9) must be wide enough to allow liquid through, but narrow enough to prevent the indicating float exiting the indicating chamber (9) at high flow rates.

In regular intravenous liquid administration or 'drip' sets, the operator manually squeezes the drip chamber to force air into the supply container and upon release this starts the flow of liquid and allows the filling of the drip chamber. Having described the features of the present invention, it should be pointed out that it is not necessary to squeeze the design of the present invention, as the device is 'primed' to expel air by simply increasing the flow rate until the indicating chamber (9) has been filled to overflow. The device is therefore moulded from a rigid material.

Although the device herein described is intended to be used by itself in the usual infusion apparatus, it may also be used in series with other flow devices such as electrically driven pumps to monitor or set rate of flow.

While a preferred embodiment has been shown and described, it will be understood that there is no intent to limit the invention by such disclosure, but rather it is intended to cover all modifications and alternate constructions falling within the spirit and the scope of the invention as defined in the appended claims.

The invention claimed is:

1. A flow meter device comprising:
    a liquid inlet;
    a liquid outlet;
    an inlet passage that has an upper and a lower end and that is in communication at its upper end with the liquid inlet;
    an indicating chamber having a lower end that is in communication with the lower end of the inlet passage, the indicating chamber extending upwardly from its lower end to an open upper end, wherein at least part of the indicating chamber is translucent or transparent to show the height of liquid in the indicating chamber;
    an exit chamber that is in communication with the liquid outlet; and
    a flow-resistant liquid passage extending between the lower end of the inlet passage and the exit chamber and in communication with the indicating chamber, wherein the flow-resistant liquid passage provides greater resistance to liquid flow than both the inlet passage and the indicating chamber, whereby liquid can flow from the liquid inlet through the inlet passage and through the flow-resistant liquid passage into the exit chamber and from there to the liquid outlet and also from the inlet passage into the indicating chamber where it reaches a height that is in accordance with the flow of the liquid through the inlet passage,
    characterized in that:
    the device comprises two parts, a first part including the liquid outlet and the exit chamber and the second part including the liquid inlet and the inlet passage and wherein the flow-resistant liquid passage and the indicating chamber are provided between the first part and the second part; and
    the flow-resistant liquid passage is U-shaped and wherein the first part includes a bore and the second part includes a barrier located in the bore to divide the bore into separate channels that together form the U-shaped flow-resistant passage.

2. The device of claim 1 wherein the indicating chamber includes a calibrated scale to provide a measure of the height of liquid in the indicating chamber and thereby a measure of the flow of liquid through the inlet passage.

3. The device of claim 1 wherein the length of the inlet passage and its communication with the indicating chamber and with the flow-resistant liquid passage is such that no drops form when liquid flows through the liquid inlet passage, flow-resistant liquid passage and indicating chamber.

4. The device of claim 1,
    wherein the outlet end of the flow-resistant liquid passage is positioned above the level of the liquid outlet and
    wherein the volume of the indicating chamber is less than the volume of the exit chamber below the outlet end of the flow-resistant liquid passage whereby if the volume of liquid contained in the full indicating chamber flows into the exit chamber, the resulting liquid level in the exit chamber is less than the height of the outlet end of the flow-resistant liquid passage in the exit chamber such that liquid cannot flow back through the flow-resistant liquid passage when liquid flow through the liquid inlet is stopped and the liquid levels reach equilibrium.

5. The device of claim 1 wherein the U-shaped flow-resistant liquid passage has an outlet end and an inlet end that are at approximately at the same height when the device is arranged vertically, such that liquid remains in the passage when no liquid is flowing through the device, thereby inhibiting the flow-resistant liquid passage from drying out.

6. The device of claim 5 wherein the inlet and outlet ends of the flow-resistant liquid passage are chamfered such that liquid remains there when the device is at rest with no liquid flowing through the device.

7. The device of claim 1 wherein the cross-sectional area of the indicating chamber is sufficiently narrow to ensure that flow rate changes set by the operator result in a rapid corresponding change in liquid height, yet sufficiently wide to mitigate against the effects of capillary action.

8. The device of claim 1 wherein the cross-sectional area and length of the flow-resistant liquid passage provide sufficient resistance to flow to result in a discernible change of liquid head in the indicating chamber when the flow rate through the device is 0-250 ml/hour.

9. The device of claim 1 wherein the inlet passage, the indicating chamber and the flow-resistant liquid passage all extend substantially in the vertical direction when the device is orientated vertically.

10. The device of claim 1 wherein the inlet passage, the indicating chamber and the flow-resistant liquid passage allow the flow of liquid without permitting drops to form during flow.

11. The device of claim 1 wherein the overflow from the indicating chamber may be so shaped as to form drops as liquid flows into the exit chamber to allow flow rates higher than those measured in the indicating chamber to be measured using the current method of drop counting.

12. The device of claim 1, wherein the device has an outer wall which is part of the first part and wherein the indicating chamber is formed between the second part and the outer wall, which outer wall is optionally made of a translucent or transparent material.

13. The device of claim 1, wherein the indicating chamber contains a visible float to facilitate the reading of liquid level in the indicating chamber and therefore the liquid flow rate.

14. The device of claim 1, wherein the inlet passage is fitted with a filter at its lower outlet and/or the outlet accommodates a filter.

15. The device of claim 1, wherein the first part is inserted into the second part.

16. The device of claim 15, wherein each part is a two-piece moulding.

* * * * *